United States Patent
Childers

(10) Patent No.: US 9,114,156 B2
(45) Date of Patent: *Aug. 25, 2015

(54) ENHANCED ANTIMICROBIAL SKIN PREPARATION

(75) Inventor: David A. Childers, Huntington, WV (US)

(73) Assignee: Aplicare, Inc., Meriden, CT (US)

( * ) Notice: Subject to any disclaimer, the term of this patent is extended or adjusted under 35 U.S.C. 154(b) by 997 days.

This patent is subject to a terminal disclaimer.

(21) Appl. No.: 11/971,522

(22) Filed: Jan. 9, 2008

(65) Prior Publication Data

US 2008/0102053 A1    May 1, 2008

Related U.S. Application Data

(63) Continuation-in-part of application No. 10/248,242, filed on Dec. 30, 2002.

(51) Int. Cl.
*A61K 31/79* (2006.01)
*A61K 33/18* (2006.01)

(52) U.S. Cl.
CPC ............... *A61K 31/79* (2013.01); *A61K 33/18* (2013.01)

(58) Field of Classification Search
None
See application file for complete search history.

(56) References Cited

U.S. PATENT DOCUMENTS

| | | | |
|---|---|---|---|
| 4,584,192 A | 4/1986 | Dell | |
| 5,137,718 A | 8/1992 | Gillespie | |
| 5,276,079 A * | 1/1994 | Duan et al. | 524/386 |
| 5,916,882 A | 6/1999 | Jeng | |
| 5,922,314 A | 7/1999 | Hoang | |
| 6,228,354 B1 * | 5/2001 | Jeng | 424/78.07 |
| 6,261,577 B1 * | 7/2001 | Kessler | 424/401 |
| 6,468,550 B1 * | 10/2002 | Remy | 424/401 |
| 8,206,696 B2 * | 6/2012 | Childers | 424/78.24 |
| 2002/0006383 A1 * | 1/2002 | Anderson et al. | 424/40 |
| 2003/0152644 A1 * | 8/2003 | Modak et al. | 424/667 |
| 2004/0052746 A1 | 3/2004 | Tamareselvy et al. | |
| 2004/0126355 A1 * | 7/2004 | Childers | 424/78.24 |

* cited by examiner

*Primary Examiner* — Carlos Azpuru
*Assistant Examiner* — Casey Hagopian
(74) *Attorney, Agent, or Firm* — Erin Collins

(57) ABSTRACT

An antimicrobial skin composition comprised of an antimicrobial agent, an alcohol, one or more pH sensitive viscosity builders, a plasticizer and water. Preferably, the viscosity builders of the present invention are comprised of pH sensitive methacrylic polymers which are alcohol compatible and have pH controlled water solubility. The composition combines the advantages of an antimicrobial agent and an alcohol, and has a viscosity of from 100 cp to 1,000. This viscosity is sufficiently low for purposes of dispensing and applying the preparation, yet sufficiently high to cause the solution to remain in the area of the wound and not flow away or pool under the patient. The preparation further forms a water-resistant film that is difficult to remove during wound irrigation, but can be easily removed upon completion of the procedure. In addition, the preparation is fast drying so as to take advantage of the fast high initial kill properties of alcohol. Finally, with the addition of a plasticizer (such as PEG 400), the film formed by the composition resists flaking in medical procedures requiring substantial skin manipulation.

15 Claims, No Drawings

ENHANCED ANTIMICROBIAL SKIN PREPARATION

CROSS-REFERENCE TO RELATED APPLICATION

This is a continuation in part of U.S. patent application Ser. No. 10/248,242, filed Dec. 30, 2002 entitled "Antimicrobial Skin Preparation."

BRIEF SUMMARY

This invention relates to antimicrobial skin preparations. More specifically, it relates to PVP-I/alcohol preparations that are easy to apply but resist flow after application, are fast drying, and form water-resistant but easily removable films.

Antimicrobial skin preparations function to reduce skin infection in surgical and other wounds, including needle punctures. The application of antimicrobial preparations to wounds has become standard practice in hospitals, surgery centers, and medical test laboratories. This application is generally carried out through the use of swabs or sponges to deliver the liquid antimicrobial preparation to the skin. The preparations may be prepared for use in a pre-packaged form (i.e., liquid and swab in a sealed package) or as a separate bottled liquid. Multiple applications of antimicrobial skin preparations are often required, with the preparation either being allowed to dry or blotted dry between applications. Since most current antimicrobial skin preparations are water soluble, reapplication is often necessary after the wound is irrigated with water.

Antimicrobial skin preparations are well known in the art, including those containing iodine complexed with a polymer (iodophors). The polymer is most often polyvinyl pyrrolidone (povidone). Iodophor preparations typically contain about 7.51-10% by volume of the iodine complex; povidone-iodine (PVP-I) solution is one of the most widely accepted preoperative antimicrobials. Solutions containing 5-10% PVP-I are generally recognized as safe. PVP-I solutions form a durable yet water soluble antimicrobial film when dry, and therefore resist pre-mature removal while permitting easy removal with water and mild rubbing. However, most existing iodophor skin preparations are low-viscosity liquids that tend to flow freely after application into areas remote from the wound site. This creates a need for extra care during application and increases the potential for irritation caused by solution pulling under the patient. A product that eliminates the flow problems associated with low-viscosity PVP-I solution is povidone-iodine gel (PVP-I gel). PVP-I gel is made by adding a cellulose gel, such as hydroxyethylcellulose, to PVP-I to greatly increase its viscosity to at least 8,000 cp. A PVP-I solution that is gelled with hydroxyethylcellulose is detailed in U.S. Pat. No. 5,137,718. In order to increase the initial kill of bacteria, alcohol can be added to PVP-I gel, as described in U.S. Pat. No. 5,916,882. Gelled PVP-I and PVP-I/alcohol solutions are flow-resistant compositions; however, as a result they are more difficult to dispense and apply than a low viscosity PVP-I solution. Furthermore, solutions in gel form dry slowly, which increases application time and reduces the benefits of the fast acting antimicrobial properties of alcohols in the PVP-I/alcohol gel. Another inherent problem with the current hydrophilic gel preparations is that they are water-soluble and therefore readily rehydrate during wound irrigation or subjection to water-containing body fluids, causing premature removal of the film and interference with surgical drape adhesion during surgical procedures.

Water-resistant films are disclosed in U.S. Pat. Nos. 6,228,354, 5,922,314 and 4,584,192, but the skin preparations that produce these films are low-viscosity and suffer from the flow/pulling problems discussed above. The PVP-I/alcohol solution disclosed in U.S. Pat. No. 6,228,354 has a faster drying time than the PVPI/alcohol gel, thus taking full advantage of the fast acting antimicrobial properties of alcohol in conjunction with PVP-I. The solution further eliminates interference with surgical drape adhesion caused by gel, and has controlled moisture resistance thereby reducing the likelihood of premature removal by irrigation during procedures. However, in addition to its low viscosity, the film can only be removed with an aqueous alkaline solution and physical rubbing. Similarly, the composition of U.S. Pat. No. 4,584,192 is resistant to removal with water, and can only be removed by certain alcohols which irritate compromised skin.

Finally, most prior art antimicrobial skin preparations use water as a solvent, which slows their drying rate, resulting in slow film formation, flow away from the wound site, and lengthened application process time.

It would be beneficial to have an antimicrobial skin preparation combining the advantages of an antimicrobial agent and an alcohol, which preparation has sufficiently low viscosity for ease of dispensing and application, yet sufficiently high viscosity to cause the solution to remain in the area of the wound and not flow away or pool under the patient; which forms a water-resistant film that is difficult to remove during wound irrigation, but can be easily removed upon completion of the procedure; and which is fast drying so as to take advantage of the fast high initial kill properties of alcohol, limit flow away from the wound site, and decrease application time. It would be further advantageous to have such a preparation that also withstands flaking when used in a medical procedure requiring substantial skin manipulation at the area of application (for example, breast augmentation). Prior to this invention, no single product has been developed to combine the advantages of the various current antimicrobial skin preparations as discussed above.

SUMMARY OF INVENTION

The present invention is an antimicrobial skin preparation having a viscosity of 100 cp to 1000 cp, combining the advantages of an antimicrobial agent and an alcohol. This viscosity level is sufficiently low to allow for easy application and dispensation, but sufficiently high to cause the solution to remain in the area of the wound and not flow away from the prep site or pool under the patient. In some embodiments, the composition has a viscosity of between 150 and 700 cps, preferably between 200 and 400 cps, and in certain embodiments between about 200 and 300 cps. The viscosity measurements referred to above are made at 25° C. with a Brookfield Viscometer Model LVF, using spindle 2 at 30 rpm.

The solution of the present invention further forms a water-resistant film that is difficult to remove during wound irrigation, and has comparable low potential for rehydration or interference with surgical drape adhesion as standard PVP-I solutions. However, the solution can be easily removed upon completion of the procedure with water and moderate rubbing.

Additionally, the solution of the present invention is fast drying so as to take advantage of the fast high initial kill properties of alcohol, limit flow away from the wound site, and decrease application time.

The solution is further formulated to provide a high level of efficacy with minimum required active concentration, thus reducing solution cost and minimizing irritation. The solution is effective and safe for use on intact skin in single step preparation of phlebotomy, I.V., and surgical sites.

The antimicrobial skin composition of the present invention is comprised of an antimicrobial agent, an alcohol, one or more pH sensitive viscosity builders and water. Surfactants, skin irritation reducers, and buffers may also be included. The active ingredients of the present invention are generally recognized as safe. The use of a pH sensitive viscosity builder eliminates the slow drying and re-hydration problems associated with gel forms of PVP-I and PVP-I/alcohol preparations.

In certain embodiments where the preparation will be used in medical procedures requiring significant skin manipulation, a plasticizer may be added to the composition.

DETAILED DESCRIPTION OF PREFERRED EMBODIMENTS OF THE INVENTION

The antimicrobial skin composition of the present invention is comprised of, in its most general form, an antimicrobial agent, an alcohol, one or more pH sensitive viscosity builders and water. Preferably, the antimicrobial agent is complexed with a polyvinyl lactam, and more preferably the antimicrobial agent constitutes PVP-I. Suitable alcohols for the solution of the present invention include but are not limited to ethanol and isopropanol. Isopropanol is preferred, as it is more efficient than ethanol in dissolving skin oils.

The viscosity builders in the solution are alcohol compatible and have pH controlled water solubility, and are preferably methacrylic polymers. The preferred viscosity builders include acidic acrylic polymers such as acrylates/C10-30 alkyl acrylate crosspolymer, acrylates/beheneth-25 methacrylate copolymer, acrylates copolymer, acrylates/steareth-20 methacrylate copolymer and carbomer. A more preferred viscosity builder is the Acrylates/Steareth-20 Methacrylate Copolymer, which is available under the trade name of ACULYN™ 22 from Rohm and Haas. ACULYN™ 22 (acrylates/steareth-20 methacrylate copolymer) is supplied by Rohm and Haas at a polymer solids concentration of 30%, with a pH of about 3.0. Acidic acrylic polymers normally function as viscosity builders that become more water-soluble as they are neutralized; the water solubility thereof is limited in the present invention because of the relatively low pH of the solution. While the polymer is insoluble in water at low pH, it is compatible with alcohol regardless of the pH level thereof, and therefore the polymer is especially suitable in the low pH solution of the present invention. Furthermore, viscosity builders having pH controlled water solubility decrease the water solubility of the prep film of the present invention, but allow for easy removal by mild physical rubbing. The main mechanism of ACULYN™ 22 (acrylates/steareth-20 methacrylate copolymer) in building viscosity for the solution of the present invention is its associative thickening properties, caused by physical forces between particles of ACULYN™ 22 (acrylates/steareth-20 methacrylate copolymer) and the solution.

Preferably, the solution contains 5-10% by weight complexed antimicrobial agent, 60-95% by volume alcohol, 1-5% by solids weight polymer pH sensitive viscosity builder, and water. As regards the alcohol, when using ethanol it should comprise about 60-95% of the volume of the entire solution, whereas isopropanol should comprise about 70-91.3% of the volume of the entire solution. The preferred solution has a pH range from about 1.5 to 6.5, and a specific gravity range of about 0.790 to 0.990 depending upon the applicable concentrations of the actives and excipient, if any. The solution of the present invention may also include a skin irritation reducer (e.g., glycerin), a surface tension adjuster (e.g., a nonionic surfactant such as Nonoxynol-9), a synergistic secondary thickener (e.g., polyvinyl pyrrolidone), acid and base pH adjusters (e.g., phosphoric acid and aminomethyl propanol), buffers and/or additional viscosity builders.

A more preferred embodiment of the invention has a pH of approximately 3-4, and includes about 5-10% by weight PVP-I; about 70-91% by volume isopropanol; about 0.2%-0.3% by weight aminomethyl propanol; about 0.01% to 1.0% by weight phosphoric acid; 0.1%-5% by weight glycerin; 0.1% to 1.0% by weight non-ionic surfactant Nonoxynol-9; and 2%-4% pH sensitive methacrylic polymer viscosity builder selected from acidic acrylate polymers which are commonly used as viscosity builders.

Another preferred antimicrobial skin preparation embodiment of the present invention comprises, by weight: 7.5% PVP-I, 0.75% available iodine (USP/EP Grade); 64.5% isopropanol (USP/EP Grade); 2.4% acrylates/steareth-20 methacrylate copolymer; 0.27% aminomethyl propanol 95%; 0.06% phosphoric acid (75%); and water. The pH of this preferred embodiment of the present invention is about 3.5, the viscosity is about 250 cp, and the specific gravity is about 0.889.

When the preparation of the present invention is intended for use in a medical procedure requiring substantial skin manipulation at the area of application, the preparation has been found to flake after drying and during the manipulation of the skin. Therefore, your inventor has determined that under these conditions, the preparation may further require a plasticizer. The plasticizer should be alcohol soluble or miscible, and should be selected so that it does not diminish the stability of the anti-microbial agent. More preferably, the plasticizer is polyethylene glycol; your inventor specifically prefers polyethylene glycol having a molecular weight of 380-420 g/mole (PEG-400). Your inventor has discovered that PEG-400 provides excellent film flexibility in the preparation of the present invention, without affecting drying time or water solubility. This discovery was unanticipated since it was believed that PEG-400 (and presumably other polyethylene glycols) would not function as a plasticizer with acrylates in alcohol (PEG 400 is used as a plasticizer for other povidone and PVP-I solutions). However, your inventor found good compatibility with the composition of the present invention, even after storage at high (60° C.) and low (−15° C.) temperature extremes. Furthermore, after the solution dried, the polyethylene glycol did not recoalesce.

The plasticizer may be added to the formula in a w/w range of 1% to at least 3.5%. The amount of plasticizer added will vary depending on the plasticizer used, with the intent of providing sufficient flexibility to the film, while substantially maintaining the antimicrobial, viscosity, water solubility and fast drying characteristics of the original embodiments of the present invention. When using PEG 400 in the formulation described hereinbefore (see paragraph [0018]), the plasticizer is most preferably present at 3.38% w/w of the preparation, replacing the water; however, in order to maintain the relative viscosity and pH of this preferred formulation, the percent of acrylate thickner in composition was decreased to 2.32% and the aminomethyl propanol was decreased to 0.265%.

Testing of Formulations.

Three formulations of the present invention described herein were tested. The first formulation tested (Formula 1) was the preferred antimicrobial skin preparation embodiment of the present invention described in paragraph [0018]. The second preparation (Formula 2) contained 7.5% PVP-I, 0.75% available iodine (USP/EP Grade); 64.5% isopropanol (USP/EP Grade); 2.4% acrylates/steareth-20 methacrylate copolymer; 0.27% aminomethyl propanol 95%; 0.06% phosphoric acid (75%); 3.5% PEG 400; and water. The third formulation (Formula 3) contained the same ingredients as Formula 2, but had 3.5% of glycerin in lieu of PEG 400.

These formulations were tested for visual coat cracking; wetting and dripping time; viscosity; drape adhesion/ability to write on prep/removal; solution dry time; running/pooling analysis; and amount of flaking during tension. The results of these tests follow:

Test 1—Visual Coat Cracking.

In this test, solutions were coated onto 1"×5" strips of 2 mil PE and put onto Instron testile strength testing equipment at a cross head speed of 2"/minute. The Instron was stopped when noticeable cracking was observed, or the strip broke. Then the maximum disbursement displacement at cracking/break of PE was measured.

|  | Displacement (inches) |
| --- | --- |
| Formula 1 | 1" |
| Formula 2 | 8" |
| Formula 3 | 7" |

While Formula 1 showed cracking at a displacement level of 1", Formulas 2 and 3 both broke at their respective displacement level prior to showing signs of cracking.

These levels were also measured as a percentage of stretch, with Formula 1 flaking at 200% stretch with cracking. The other formulations did not break in these stretch tests of up to 210% stretch, or stretch and crack.

Test 2—Wetting and Dripping time.

In this evaluation, full applicators were made with the formulas. Ten vials of each Formula were run through a sterilization stimulation and then tested. After sterilization, applicators were held perpendicular to the floor (with a sponge at one end thereof, closest to the floor) and timed for wetting time (time that solution is first noticeable on bottom of sponge) and dripping time (time that first drip drops from the sponge). The average times for each Formula are presented in the following table:

|  | Wetting (sec.) | Drip (sec.) |
| --- | --- | --- |
| Formula 1 | 11.716 | 17.950 |
| Formula 2 | 14.646 | 29.465 |
| Formula 3 | 13.529 | 28.228 |

Test 3—Viscosity Testing.

Using a Brookfield viscometer in a wet lab, with a volume of 220 milliliters, temperature at 60-61° F., spindle RV-2, using RPMs of 2, 4, 10, 20 and 30, respectively, the following viscosity values were measured in each Formula:

| Viscosity of Solutions (in cps) | | | | | |
| --- | --- | --- | --- | --- | --- |
|  | RPM = 2 | RPM = 4 | RPM = 10 | RPM = 20 | RPM = 30 |
| Formula 1 | 400 | 450 | 400 | 360 | 328.6 |
| Formula 2 | 500 | 450 | 420 | 380 | 328.6 |
| Formula 3 | 500 | 450 | 400 | 370 | 307.1 |

Test 4—Drape Adhesion/Write on Prep/Removal.

The three formulations were evaluated on two volunteers (P1 and P2), with one arm prepped with Formula 1, and the other arm of each volunteer prepped with Formulas 2 or 3, respectively. Six steridrape 1"×2" were adhered to each prepped arm. Three drapes from each were removed immediately following application, and three at 6 hours. After removing the drapes, OR markers were used to write on the solution, and the subject was asked to remove the film with soap and water.

| Drape Removal Force (gf) | | |
| --- | --- | --- |
|  | T = 0 | T = 6 hours |
| Formula 1 | 300 - P1 | 410 - P1 |
|  | 200 - P2 | 310 - P2 |
| Formula 2 | 450 - P1 | 300 - P1 |
| Formula 3 | 410 - P2 | 260 - P2 |

The solutions were able to be written on with four different OR markers after a period of 6 hours, and were able to be easily removed from the subject with soap and water.

Test 5—Solution Dry Time.

In this evaluation, 3 grams of each of the formulations were placed onto a scale, with weight measurements taken every minute. A solution was considered "dry" when the weight of the formulation remained constant for three minutes.

|  | Dry time (min.) |
| --- | --- |
| Formula 1 | 31.4 |
| Formula 2 | 30.2 |
| Formula 3 | 29.8 |

Test 6—Running/Pooling Analysis.

In this evaluation, 3 cc of each of the formulations was placed at the top of a piece of lexan plastic, inclined at 24°. At set periods of time, the distance that each solution ran was measured, with the results as follows:

|  | 60 sec. | 120 sec. | 180 sec. | 240 sec. | 300 sec. |
| --- | --- | --- | --- | --- | --- |
| Formula 1 | 9.9 in. | 13.6 in. | 16 in. | 18.1 in. | 19.3 in. |
| Formula 2 | 10.6 in. | 14.5 in. | 16.5 in. | 18.8 in. | 19.9 in. |
| Formula 3 | 11.3 in. | 14.1 in. | 17.3 in. | 19.3 in. | 20.6 in. |

Test 8—Amount of Flaking During Tension.

In this evaluation the formulations were coated onto 3"×5" vinyl and allowed to dry for an hour. The coated vinyl was placed into Intsron tensile strength testing equipment inside a plastic bag, and cycled twenty times up to 160% elongation, at a speed of 30 inches per minute. The bag was then measured for the amount of film that flaked off of the vinyl.

|  | Percent of coating removed |
| --- | --- |
| Formula 1 | 62% |
| Formula 2 | 0% |
| Formula 3 | 0% |

Manufacture.

The composition of the present invention is preferably manufactured by combining a minimal amount of the alcohol and sufficient amount of the water to provide volume to blend in the antimicrobial agent, if the same is provided in powdered form. As there is some risk of ignition of suspended dust particles when adding a powdered antimicrobial agent, the preliminary alcohol content should be minimal and the dust particles should be added to avoid forming a cloud of finely dispersed particles over the batch. The viscosity builder is then preferably diluted in water and added slowly to the solution. Any additional alcohol can then be added to the solution, as well as any desirable elements such as glycerin and base pH adjusters. Each element should be added slowly, and mixed well into the solution so that the solution is homogeneous prior to the addition of a subsequent element. If a plasticizer is included in the preparation, it can be added at any step of the manufacturing process.

I claim:

1. An antimicrobial skin preparation prepared by a process comprising the steps of:
   A. applying an antimicrobial composition to skin wherein the composition consists of: povidone-iodine; one or more alcohol; one or more pH sensitive acrylic polymers in an amount sufficient to build the viscosity of the composition in solution to between about 100 to 1,000 cps (measured at 25° C. with a Brookfield Viscometer Model LVF, using spindle 2 at 30 rpm); and optionally, one or more components selected from the group consisting of: skin irritation reducers, pH adjusters, water, buffers and any combinations thereof, wherein the pH of the composition is between about 1.5 and 4;
   B. allowing the composition to dry on the skin and form a flexible film, wherein said flexible film resists flaking and cracking during a medical procedure; and
   C. removing the flexible film after completion of the medical procedure.

2. The antimicrobial skin preparation of claim 1, wherein the alcohol is chosen from the group consisting of ethanol and isopropanol.

3. The antimicrobial skin preparation of claim 1, wherein the pH adjuster, phosphoric acid, is present in the preparation.

4. The antimicrobial skin preparation of claim 1, wherein the pH sensitive acrylic polymers are chosen from the group consisting of: acrylates/C10-30 alkyl acrylate crosspolymer, acrylates/beheneth-25 methacrylate copolymer, acrylates copolymer, acrylates/steareth-20 methacrylate copolymer and carbomer.

5. The antimicrobial skin preparation of claim 4, wherein the pH sensitive acrylic polymer is acrylates/steareth-20 methacrylate copolymer.

6. The antimicrobial skin preparation of claim 1, wherein the viscosity of the composition is between 150 and 700 cps (measured at 25° C. with a Brookfield Viscometer Model LVF, using spindle 2 at 30 rpm).

7. The antimicrobial skin preparation of claim 1, wherein the composition contains about 5-10% by weight of povidone-iodine.

8. The antimicrobial skin preparation of claim 1, wherein the pH of the composition is from about 3 to 4.

9. The antimicrobial skin preparation of claim 1, wherein the composition contains about 60-95% by volume of said one or more alcohols.

10. The antimicrobial skin preparation of claim 1, wherein a skin irritation reducer is present in the preparation.

11. The antimicrobial skin preparation of claim 1, wherein the composition contains about 1-5% by solids weight of said pH sensitive acrylic polymer.

12. An antimicrobial skin preparation prepared by a process comprising the steps of:
    A. applying an antimicrobial composition to skin wherein the composition consisting of: (a) 5-10% by weight povidone-iodine; (b) 60-95% by volume alcohol; (c) 1-5% by solids weight one or more pH sensitive acrylic polymers in an amount sufficient to build the viscosity of the composition in solution to between about 100 to 1,000 cps (measured at 25° C. with a Brookfield Viscometer Model LVF, using spindle 2 at 30 rpm); (d) optionally, one or more optional components selected from the group consisting of: skin irritation reducers, nonionic surfactants, pH adjusters, buffers and any combinations thereof; and (e) water; wherein the pH of the composition is between about 3 and 4;
    B. allowing the composition to dry on the skin and form a flexible film;
    C. irrigating a wound and the flexible film surrounding the wound;
    D. removing the flexible film after completion of the medical procedure.

13. The antimicrobial skin preparation of claim 12, wherein the alcohol is isopropanol and is contained at 70-91.3% by volume.

14. The antimicrobial skin preparation of claim 12, wherein the pH sensitive acrylic polymer is acrylates/steareth-20 methacrylate copolymer.

15. The antimicrobial skin preparation of claim 12, wherein the viscosity of the composition is between 150 and 700 cps (measured at 25° C. with a Brookfield Viscometer Model LVF, using spindle 2 at 30 rpm).

* * * * *